US010912621B2

(12) United States Patent
Chua

(10) Patent No.: US 10,912,621 B2
(45) Date of Patent: *Feb. 9, 2021

(54) STOCKINETTE HAVING FOLDED STRUCTURE FOR SIMPLIFIED APPLICAITON

(71) Applicant: Medline Industries, Inc, Northfield, IL (US)

(72) Inventor: Mark Spencer G. Chua, Northbrook, IL (US)

(73) Assignee: Medline Industries Inc., Northfield, IL (US)

( * ) Notice: Subject to any disclaimer, the term of this patent is extended or adjusted under 35 U.S.C. 154(b) by 392 days.

This patent is subject to a terminal disclaimer.

(21) Appl. No.: 15/718,994

(22) Filed: Sep. 28, 2017

(65) Prior Publication Data

US 2018/0014898 A1  Jan. 18, 2018

Related U.S. Application Data

(63) Continuation of application No. 12/537,961, filed on Aug. 7, 2009, now Pat. No. 9,808,319.

(51) Int. Cl.
   *A61B 46/27* (2016.01)

(52) U.S. Cl.
   CPC ..................... *A61B 46/27* (2016.02)

(58) Field of Classification Search
   CPC ......... A61B 46/10; A61B 46/13; A61B 46/17; A61B 46/20; A61B 46/30; A61B 46/47; A61B 2046/236; A61B 11/00; A61B 11/003; A61B 11/10; A61F 15/004
   See application file for complete search history.

(56) References Cited

U.S. PATENT DOCUMENTS

| 2,664,570 | A | * | 1/1954 | Artzt ................. A41D 15/002 2/78.3 |
| 2,825,902 | A | | 3/1958 | Breier |
| 2,971,198 | A | | 2/1961 | Tomich |
| 3,144,661 | A | | 8/1964 | Buser |
| 3,359,569 | A | | 12/1967 | Scrivens |
| 3,429,433 | A | | 2/1969 | Holt |
| 3,540,441 | A | | 11/1970 | Collins |
| 3,625,206 | A | | 12/1971 | Charnley |

(Continued)

OTHER PUBLICATIONS

Bravo, Jocelyn , "NonFinal OA", U.S. Appl. No. 14/086,798, filed Nov. 21, 2013; Mailed May 20, 2019.

(Continued)

*Primary Examiner* — Rachael E Bredefeld
*Assistant Examiner* — Camtu T Nguyen
(74) *Attorney, Agent, or Firm* — Philip H. Burrus, IV

(57) ABSTRACT

A stockinette (200), suitable for covering an appendage (1440) of a patient, includes one or more folds (206). The fold (206) can be in a length of material (205) disposed between an open end (204) and a closed end (203). Alternatively, the fold (880) can be in an optional cuff (860) formed by a section of material (661) near the open end (603). Folds can be present both in the length of material (205) and in the cuff (860) as well. The cuff (860) can be disposed atop the fold (206) in the length of material (205). The stockinette (200) enables one person to apply the stockinette (200) to an appendage (1440) with one continuous motion that expands the folds.

18 Claims, 9 Drawing Sheets

(56) References Cited

U.S. PATENT DOCUMENTS

| | | | |
|---|---|---|---|
| 3,707,964 | A | 1/1973 | Patience et al. |
| 3,721,999 | A | 3/1973 | Goya et al. |
| 3,858,243 | A | 1/1975 | Pierron et al. |
| 3,935,596 | A | 2/1976 | Allen, Jr. et al. |
| 3,968,792 | A | 7/1976 | Small |
| 3,989,040 | A | 11/1976 | Lofgren et al. |
| 4,000,521 | A | 1/1977 | Zoephel et al. |
| 4,119,093 | A * | 10/1978 | Goodman ............... A61B 46/27 128/856 |
| 4,153,054 | A | 5/1979 | Boone |
| 4,214,320 | A | 7/1980 | Belkin |
| RE30,520 | E | 2/1981 | Pierron |
| 4,308,864 | A | 1/1982 | Small et al. |
| 4,315,334 | A | 2/1982 | Pearsall |
| 4,467,477 | A | 8/1984 | DeGennaro |
| 4,523,335 | A | 6/1985 | Scrivens |
| 4,561,126 | A | 12/1985 | Truman |
| 4,631,756 | A | 12/1986 | Scrivens |
| 4,674,132 | A | 6/1987 | Stein et al. |
| 4,705,171 | A | 11/1987 | Eldridge |
| 4,783,854 | A | 11/1988 | Bjorklund |
| 4,864,657 | A | 9/1989 | Lake |
| 4,905,710 | A * | 3/1990 | Jones ............... A61B 46/00 128/849 |
| 4,942,987 | A | 7/1990 | Stackhouse |
| 5,010,592 | A | 4/1991 | Skiles, Jr. |
| 5,029,344 | A | 7/1991 | Shannon et al. |
| 5,033,115 | A | 7/1991 | Bowling et al. |
| 5,061,246 | A | 10/1991 | Anapliotis |
| 5,097,534 | A | 3/1992 | Viemeister et al. |
| 5,253,642 | A | 10/1993 | Stackhouse et al. |
| 5,362,306 | A | 11/1994 | McCarver et al. |
| 5,433,221 | A * | 7/1995 | Adair ............... A61B 46/10 128/849 |
| 5,533,209 | A | 7/1996 | Davis |
| 5,605,534 | A * | 2/1997 | Hutchison ............ A61F 13/041 128/849 |
| 5,674,189 | A | 10/1997 | McDowell et al. |
| 5,784,718 | A | 7/1998 | Finnegan |
| 5,862,525 | A | 1/1999 | Tankersley et al. |
| 5,867,825 | A | 2/1999 | Scheerer |
| 5,985,395 | A | 11/1999 | Comstock et al. |
| 6,062,444 | A | 5/2000 | Tankersley et al. |
| 6,536,636 | B1 | 3/2003 | McDonniel |
| 7,412,728 | B2 | 8/2008 | Alesina et al. |
| 7,654,266 | B2 * | 2/2010 | Corbitt, Jr. ............. A61B 50/30 128/849 |
| 7,841,020 | B2 | 11/2010 | Mayfield et al. |
| 8,006,836 | B2 | 8/2011 | Trombetta |
| 8,069,495 | B2 | 12/2011 | Kemper |
| 8,162,137 | B2 | 4/2012 | Vellutato, Jr. et al. |
| 9,808,319 | B2 * | 11/2017 | Chua ................... A61B 46/27 |
| 2004/0019951 | A1 | 2/2004 | Cioffi |
| 2004/0103904 | A1* | 6/2004 | Auerbach ............ A61B 46/27 128/856 |
| 2004/0172734 | A1 | 9/2004 | Hartbrodt |
| 2005/0044608 | A1 | 3/2005 | Ambrose et al. |
| 2006/0117456 | A1 | 6/2006 | Griesbach |
| 2006/0236440 | A1 | 10/2006 | Zahler |
| 2006/0277668 | A1 | 12/2006 | Plut et al. |
| 2007/0061940 | A1 | 3/2007 | Cazares |
| 2008/0178365 | A1 | 7/2008 | Furgerson et al. |
| 2009/0183529 | A1 | 7/2009 | Modiano |
| 2010/0313323 | A1 | 12/2010 | Tennelle |
| 2011/0023210 | A1 | 2/2011 | Porowski |
| 2011/0024485 | A1 | 2/2011 | Porowski |
| 2011/0154554 | A1 | 6/2011 | Furlong |
| 2011/0167534 | A1 | 7/2011 | Wong et al. |
| 2012/0060257 | A1 | 3/2012 | Herzog |
| 2012/0124722 | A1 | 5/2012 | Yadav et al. |
| 2012/0312308 | A1 | 12/2012 | Allen |
| 2013/0091616 | A1 | 4/2013 | Muche et al. |
| 2013/0239290 | A1 | 9/2013 | Rossi |
| 2013/0276204 | A1 | 10/2013 | Pasko et al. |
| 2014/0007316 | A1 | 1/2014 | Tommarello et al. |
| 2014/0082816 | A1 | 3/2014 | Christopher |
| 2014/0173814 | A1 | 6/2014 | Yadav et al. |
| 2014/0215681 | A1 | 8/2014 | Goodman |
| 2015/0089712 | A1 | 4/2015 | Gamble |
| 2015/0096099 | A1 | 4/2015 | Vanneste |
| 2015/0113698 | A1 | 4/2015 | Gregersen-Brown |

OTHER PUBLICATIONS

Bravo, Jocelyn M., "NonFinal OA", U.S. Appl. No. 14/086,798, filed Nov. 21, 2013; Mailed Dec. 11, 2019.

"Final OA", U.S. Appl. No. 14/086,798, filed Nov. 21, 2013; Mailed Feb. 1, 2016.

"Medline Catalog", 2-Ply Sterile Cotton Stockinette by Alba-Waldensian; Medline Catalog; http://www.medline.com/catalog/catalog.jsp; Unknown Publication date but believed to be prior to present application filing date.

"Medline Catalog", Cotton Stockinette by Alba-Waldensian; Medline Catalog; http://www.medline.com/catalog/catalog.jsp; Unknown Publication date but believed to be prior to present application filing date.

"Medline Catalog", Single Ply Standard Stockinettes by DeRoyal; Medline Catalog; http://www.medline.com/catalog/catalog.jsp; Unknown Publication date but believed to be prior to present application filing date.

"Medline Catalog", Single-Ply Sterile Stockinettes by Kerma Medical; Medline Catalog; http://www.medline.com/catalog/catalog.jsp; Unknown Publication date but believed to be prior to present application filing date.

"Medline Catalog", Sterile Bias Cute Cuttron Stockinette by Alba-Waldensian; Medline Catalog; http://www.medline.com/catalog/catalog.jsp; Unknown Publication date but believed to be prior to present application filing date.

"Medline Catalog", Stockinette by Derma Sciences; Medline Catalog; http://www.medline.com/catalog/catalog.jsp; Unknown Publication date but believed to be prior to present application filing date.

"Medline Catalog", Strl Stockinette Cttn 1-Ply by Alba-Waldensian; Medline Catalog; http://www.medline.com/catalog/catalog.jsp; Unknown Publication date but believed to be prior to present application filing date.

"Medline Catalog", TG Stockinettes by Lohmann and Rauscher; Medline Catalog; http://www.medline.com/catalog/catalog.jsp; Unknown Publication date but believed to be prior to present application filing date.

"Medline Catalog", Tube, Luki 864304; Medline Catalog; http://www.medline.com/catalog/catalog.jsp; Unknown Publication date but believed to be prior to present application filing date.

Harris, Raymond E., "NonFinal OA", U.S. Appl. No. 12/537,961, filed Aug. 17, 2009; Mailed Jul. 17, 2012.

Harris, Raymond E., "Appeal Decision", U.S. Appl. No. 12/573,961, filed Aug. 7, 2009; dated Mar. 6, 2017.

Harris, Raymond E., "Final OA", U.S. Appl. No. 12/537,961, filed Aug. 7, 2009; Mailed Nov. 21, 2012.

Harris, Raymond E., "Final Office Action", U.S. Appl. No. 12/537,961, filed Aug. 7, 2009; dated Apr. 11, 2012.

Harris, Raymond E., "Non-Final Office Action", U.S. Appl. No. 12/537,961, filed Aug. 7, 2009; dated Nov. 9, 2011.

Harris, Raymond E., "Notice of Allowance", U.S. Appl. No. 12/537,961; filed Aug. 7, 2009; dated Oct. 6, 2017.

Wu, Jocelyn Mary, "NonFinal OA", U.S. Appl. No. 14/086,798; filed Nov. 21, 2013; Mailed Sep. 24, 2015.

* cited by examiner

STOCKINETTE HAVING FOLDED STRUCTURE FOR SIMPLIFIED APPLICAITON

CROSS REFERENCE TO PRIOR APPLICATIONS

This application is a continuation under 35 USC § 120 U.S. application Ser. No. 12/537,961, filed Aug. 7, 2009, which is incorporated by reference for all purposes.

BACKGROUND

Technical Field

This invention relates generally to a surgical stockinette that can be applied to body appendages during medical procedures, and more particularly to a surgical stockinette that is easily expanded due to its folded construction.

Background Art

A sterile environment is critical during surgery. For this reason, a patient is generally completely covered during surgery except for the portion of the body undergoing the operation. Techniques for maintaining sterile operating environments generally require that portions of a patient that are not subject to the operation should be isolated from the surgical site to reduce the risk of contamination and infection. Generally a surgical drape is therefore used to isolate the surgical site from other parts of the patient. For example, if a person is having an appendix removed, the person will generally be covered with a surgical drape to maintain integrity of the sterile field. A small portion of the person's body above the appendix will be exposed through the drape such that it is accessible to the surgeon. Alternatively, the patient can be covered entirely. The surgeon can then cut through either a fenestration in the drape or through incise material in the drape to expose the appendix region.

Matters can become complicated when operating on limbs. It may be necessary to have the person's entire leg exposed through an aperture in the surgical drape. To help maintain a sterile operating environment, a stockinette is used to cover portions of the patient's limb that is not subject to the operating procedure.

Turning now to FIG. 1, illustrated therein is one prior art surgical stockinette 100. The stockinette 100 is initially packaged in a rolled configuration, with an open end rolled back across the stockinette 100 again and again to form a ring. The stockinette 100 is applied to a patient's limb 101 by inserting the limb 101 into an open end 102 of the stockinette 100. The rolled portion 103 is then unrolled across the limb 101, thereby covering the limb 101.

The problem with this prior art stockinette 100 is that it is troublesome to apply. Application generally requires two people 104, 105 during the entire operation. A first person 104 must lift the limb 101 and hold it high in the air so that the large rolled portion 103 will fit under the limb 101. Furthermore, the second person 105 must then make numerous unrolling motions to get the stockinette 100 on the limb 101. In making these numerous unrolling motions, the second person 105 has a significantly heightened risk of touching the limb 101, thereby potentially compromising the sterile field. The application of this prior art stockinette 100 is time-consuming and cumbersome, which can result in delaying the surgical procedure.

There is thus a need for an improved stockinette.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
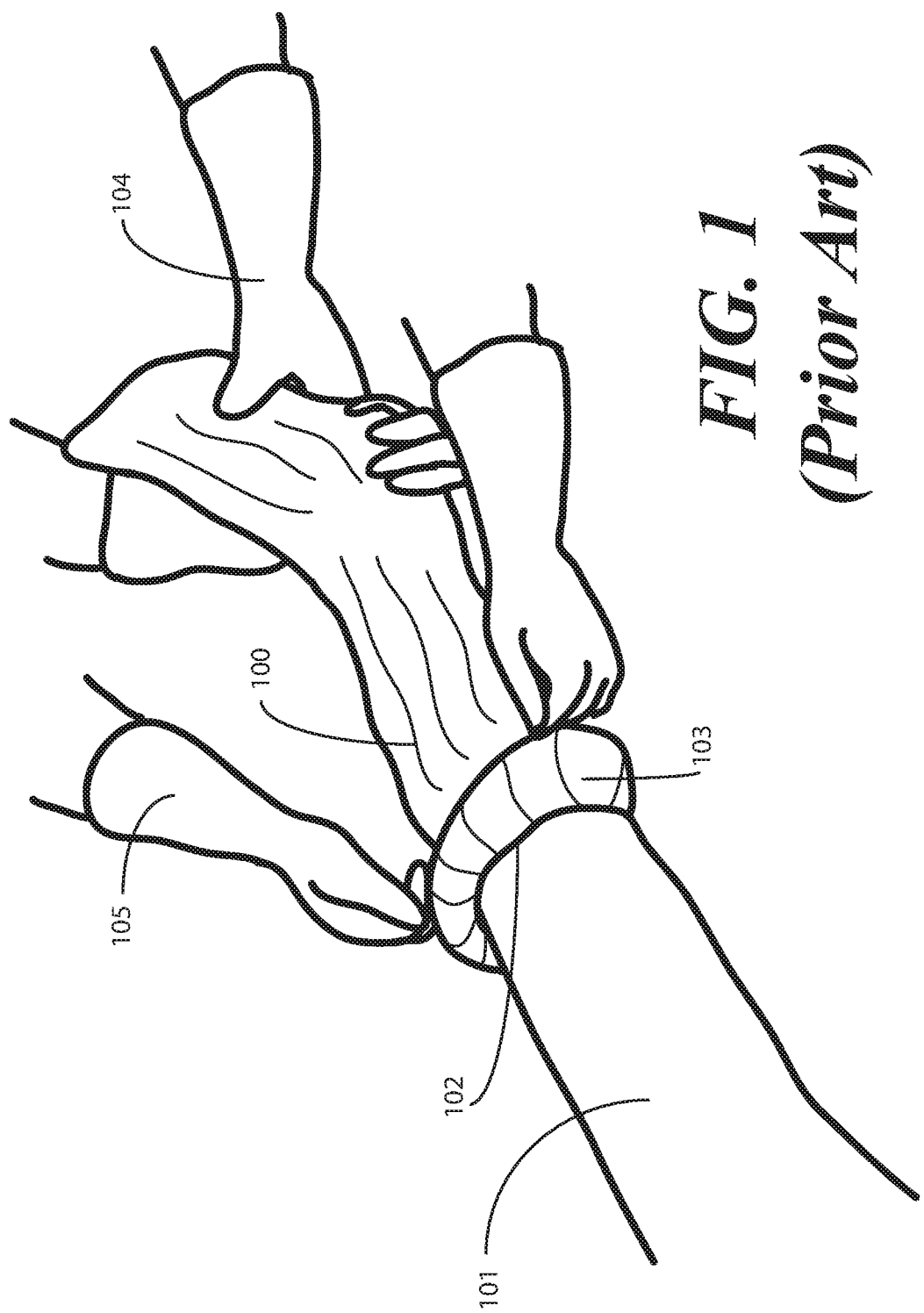
FIG. 1 illustrates a prior art stockinette.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the present invention provide a stockinette that includes a length of material disposed between an open end and a closed. The length of material, in one embodiment, is folded such that it can be easily expanded by straightening the folds. In one embodiment, the fold is an accordion-style fold. In another embodiment, the fold is a twist fold. The stockinette is configured to be easily applied to a patient by inserting an appendage into the stockinette and then pulling the stockinette along the appendage, thereby expanding the folds.

Embodiments of the present invention provide a stockinette that is folded such that it only takes one major motion to apply the stockinette to a patient's appendage. As a result, it is not necessary to hold the appendage high in the air for as long of a duration, so as to make room for a large rolled portion. Further, the person applying the stockinette need not make multiple unrolling motions during the application process, thereby reducing the risk of contaminating the sterile field. Embodiments of the present invention therefore decrease the amount of time and labor required to apply the stockinette. Additionally, some embodiments of the invention include a cuff into which a person's hands can be inserted during application, thereby further reducing the risk of contaminating the surgical site.

Figure 2:
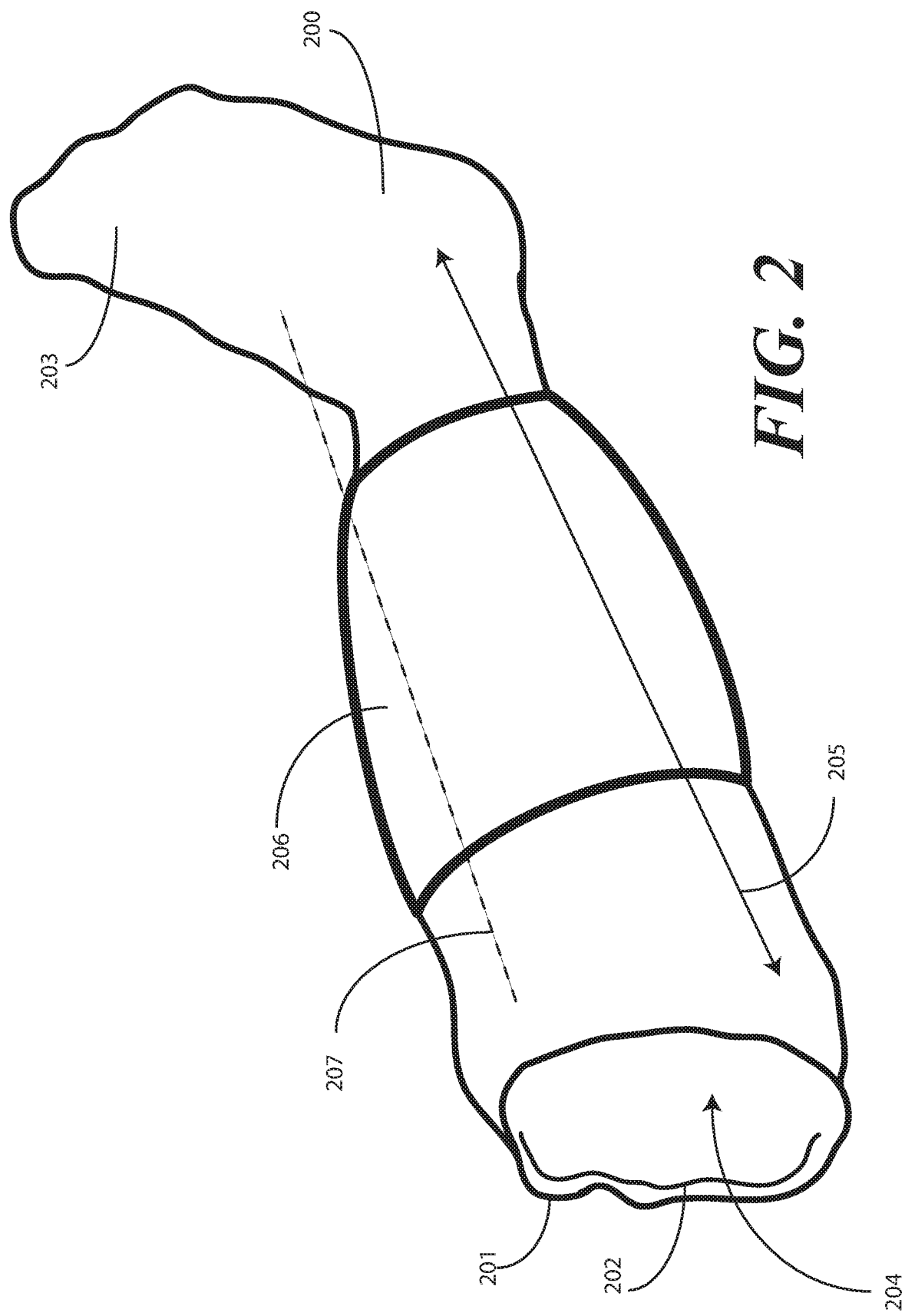
FIG. 2 illustrates a general embodiment of one stockinette in accordance with embodiments of the invention.

Turning now to FIG. 2, illustrated therein is one embodiment of a stockinette 200 in accordance with embodiments of the invention. The stockinette 200 can be used in hospitals, surgery centers, and other healthcare facilities. Exemplary applications for stockinettes in accordance with embodiments of the invention include orthopedic surgeries and other general surgical procedures. Other applications include under-cast padding, covering extremities, warming extremities, and so forth. For simplicity of discussion, the stockinette described in the various figures will be designed to cover a patient's leg. However, it will be clear to those of ordinary skill in the art having the benefit of this disclosure that the invention is not so limited. Stockinettes for other appendages, such as arms, fingers, hands, and feet, can be configured in the same way as the illustrative embodiment described herein. Further, while the stockinette shown herein includes contours, it will be clear that non-contoured, tubular stockinettes may also be configured as shown and described herein.

In one embodiment, the stockinette 200 is manufactured from a single layer of material. In such an embodiment, the stockinette 200 may be manufactured from a single layer of a synthetic material, such as polyester, or a single layer of natural material, such as cotton. In another embodiment, the stockinette 200 is manufactured from multiple layers of material. For instance, the stockinette 200 may be manufactured from multiple layers of one material, such as cotton or polyester. Alternatively, the stockinette 200 can be manufactured from multiple layers of different materials.

In one embodiment, the stockinette 200 is configured to be impervious to liquids. For example, where the stockinette 200 is manufactured from multiple separate layers, the outer layer 201 of material may be a liquid-impervious material, such as a synthetic polymer manufactured by Kraton Polymers, while the inner layer 202 is manufactured from a material that is more comfortable against the patient's skin, such as polyester or cotton. In another embodiment, the stockinette may be manufactured form a single layer of liquid-impervious material, such as a rubber or synthetic polymer material.

The stockinette 200 includes a closed end 203 and an open end 204. The closed end 203 is configured to cover the end of a patient's appendage. The open end 204 is configured to receive the appendage of the patient. Said differently, the patient's appendage is inserted into the open end 204 until the end of the appendage meets the closed end 203 of the stockinette 200. A length of material 205 separates the open end 204 and the closed end 203.

In accordance with one embodiment, the length of material 205 includes a fold 206, which is shown generally in FIG. 2 as a rectangle. The fold 206 allows the stockinette 200 to be packaged in a compact configuration, yet be applied in a single sweeping motion that causes the fold to expand, thereby allowing a majority of the length of material 205 to cover the patient's appendage. This reduces the risk of surgical site contamination when compared to prior art stockinettes, as there are fewer major motions along the appendage. Additionally, embodiments of the present invention save time during application in that fewer people and motions are required during application.

The fold 206 can be expanded by pulling the open end 204 away from the closed end, thereby allowing the length of material 205 to expand. In one embodiment, the fold 206 is an accordion fold. In another embodiment, the fold 206 is a twist fold. Where the fold 206 is an accordion fold, the fold 206 can be aligned horizontally or vertically as viewed in FIG. 2. For example, in one embodiment the fold 206 can be oriented along a reference line 207 defined between the closed end 203 and the open end 204. In another embodiment, the fold 206 can be oriented askew relative to the reference line 207, such as substantially perpendicular with the reference line 207. The term "substantially" is used because it will be rare in practice to have a perfectly orthogonal relationship. The fold 206 may be non-perpendicular with the reference line 207 by a few degrees, but will still be substantially perpendicular.

Figure 3:
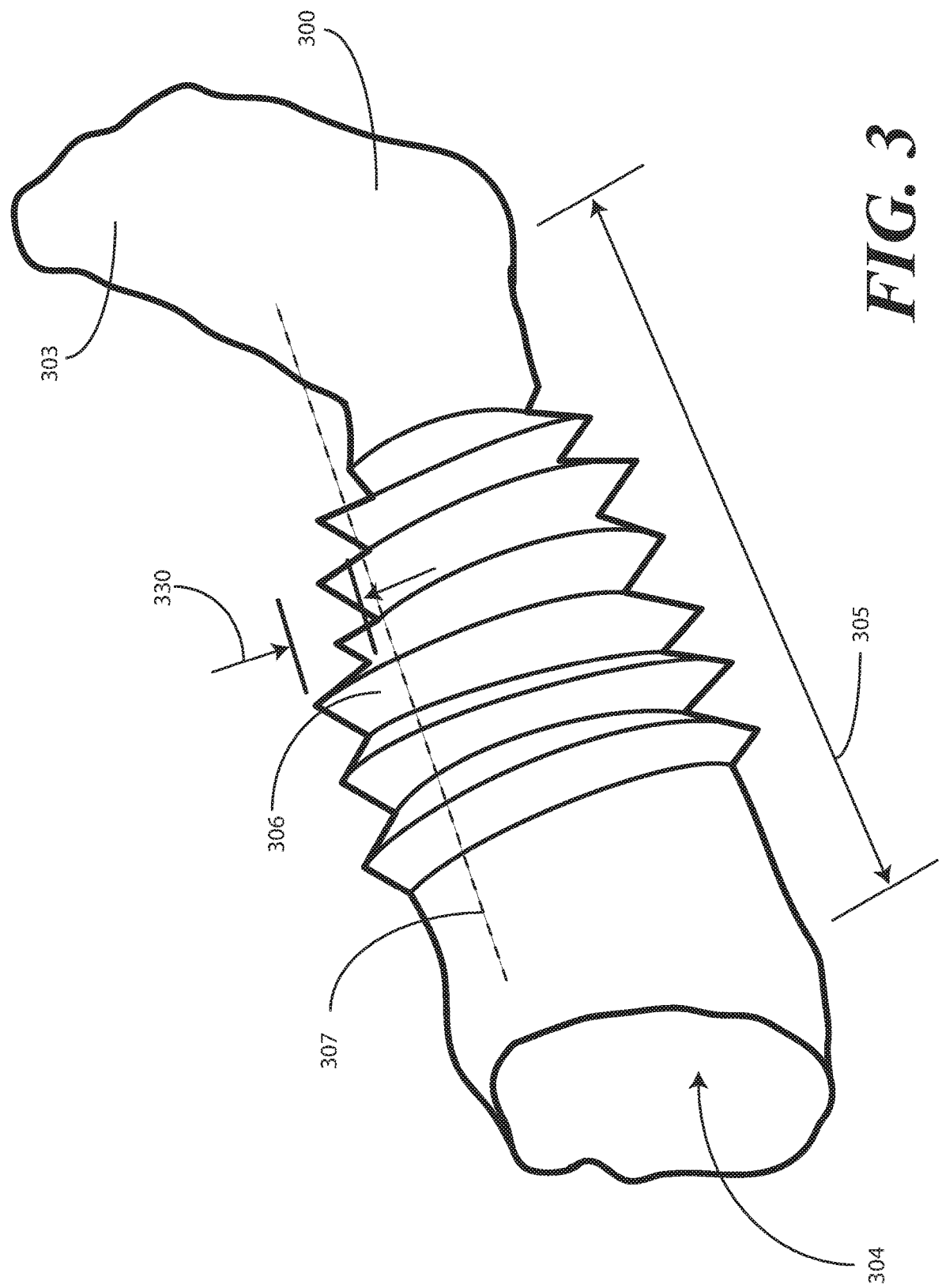
FIG. 3 illustrates one stockinette having a horizontal accordion fold in accordance with embodiments of the invention.

Turning now to FIG. 3, illustrated therein is an embodiment of a stockinette 300 that includes an accordion fold 306. The stockinette 300 is shown in a sectional view in FIG. 3.

In the embodiment of FIG. 3, the accordion fold 306 is oriented along the reference line 307 defined between the closed end 303 and the open end 304. When applied to a patient, the accordion fold 306 is expandable by pulling the open end 304 away from the closed end 303, thereby unfolding the length of material 305 disposed between the open end 304 and the closed end 303. In one embodiment, the majority of the material forming the stockinette 300 is captured within the accordion fold 306.

The accordion fold 306 can take different shapes. In one embodiment, the accordion fold will include at least twenty-five folds, with each fold having a width 330 of two inches or less. For example, if the stockinette 300 is to be used with a person's leg, and the overall stockinette 300 is four feet in length, the accordion fold 306 may have between thirty and fifty folds, with each fold having a width 330 of between one-half inch and one inch.

Figure 4:
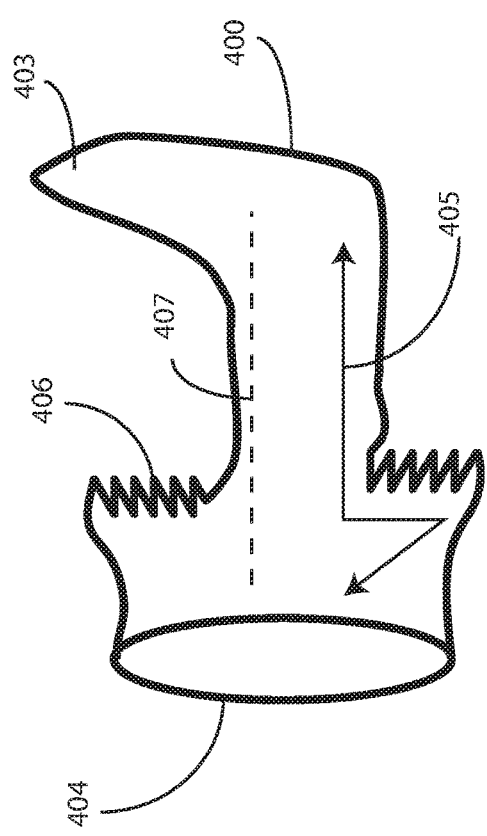
FIG. 4 illustrates one stockinette having a vertical accordion fold in accordance with embodiments of the invention.

Turning now to FIG. 4, illustrated therein is an embodiment of a stockinette 400 that includes an accordion fold 406. The stockinette 400 is shown in a sectional view in FIG. 4.

In the embodiment of FIG. 4, the accordion fold 406 is oriented askew relative to a reference line 407 defined between the closed end 403 and the open end 404. In FIG. 4, the accordion fold 406 is substantially perpendicular relative to the reference line 407. This facilitates a compact form factor from end to end.

When applied to a patient, the accordion fold 406 is expandable by pulling the open end 404 away from the closed end 403, thereby causing the accordion fold 406 to extend in a direction substantially parallel with the reference line 407. The length of material 405 unfolds between the open end 404 and the closed end 403. As with FIG. 3, the majority of the material forming the stockinette 400 can be captured within the accordion fold 406.

Figure 5:
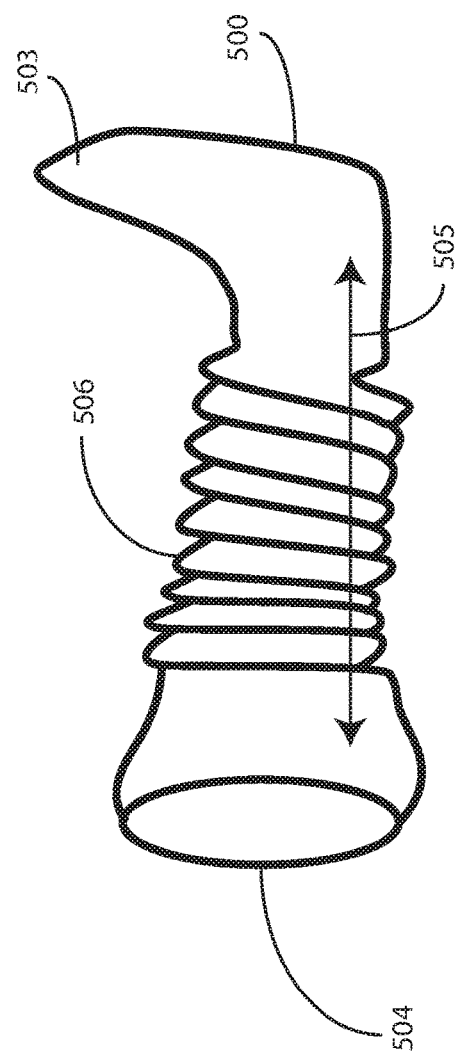
FIG. 5 illustrates one stockinette having a twist fold in accordance with embodiments of the invention.

Turning now to FIG. 5, illustrated therein is an alternate embodiment of a stockinette 500 in accordance with embodiments of the invention. In FIG. 5, rather than including an accordion fold, the stockinette 500 includes a twist fold 506. The twist fold 506 of FIG. 5 is formed by twisting and compressing the length of material 505, thereby compressing the overall stockinette 500 such that it can be easily packaged and stored.

As with previous embodiments, when applied to a patient, the twist fold 506 is expandable by pulling the open end 504 away from the closed end 503, thereby expanding the length of material 505 disposed between the open end 504 and the closed end 503. Also as with previous embodiments, the majority of the material forming the stockinette 500 can be captured within the twist fold 506 of FIG. 5.

Figure 6:
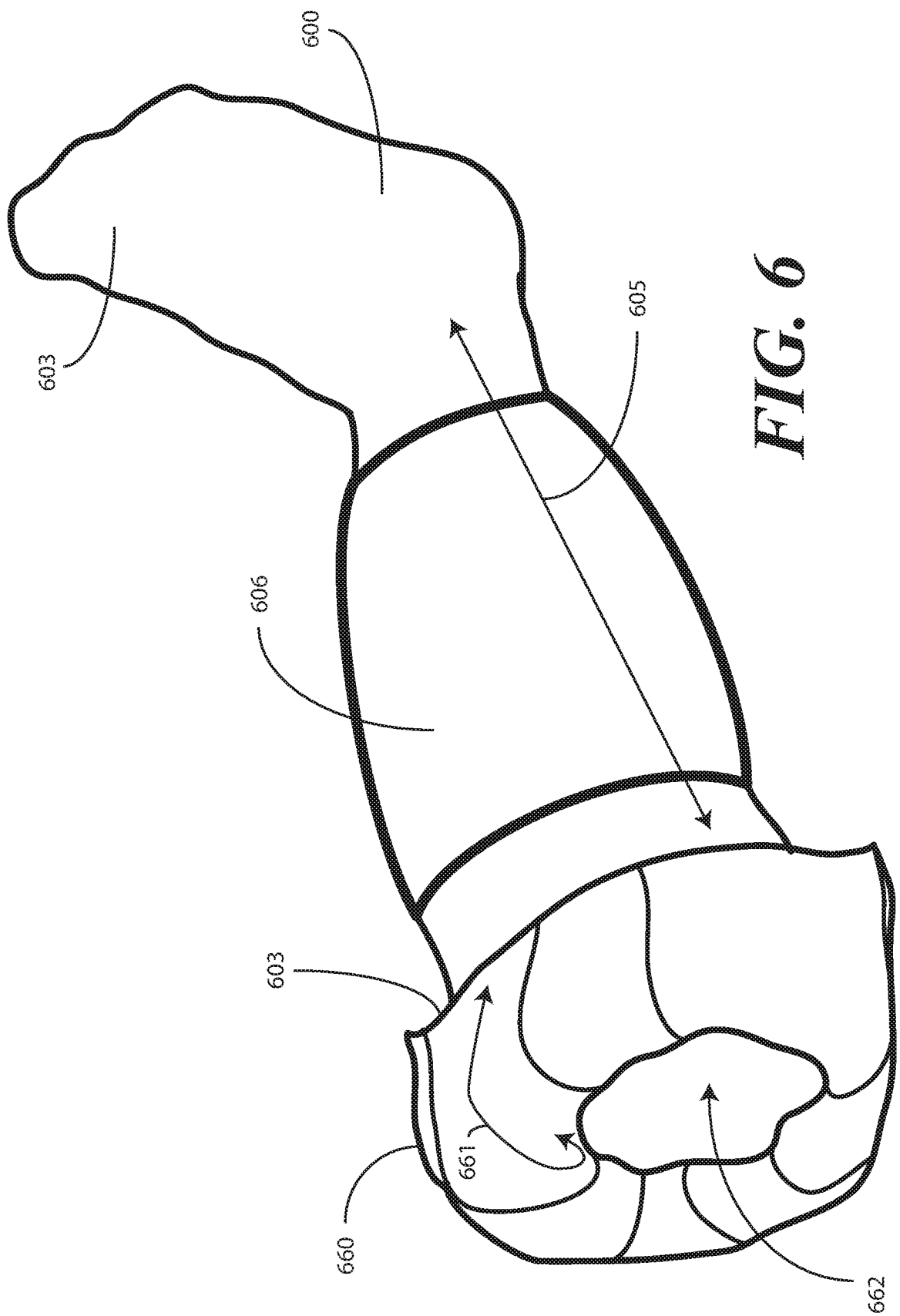
FIG. 6 illustrates one stockinette having a cuff in accordance with embodiments of the invention.

Turning now to FIG. 6, illustrated therein is another embodiment of a stockinette 600 in accordance with embodiments of the invention. The stockinette 600 of FIG. 6 is similar to that of FIG. 2, in that it includes a closed end 604, an open end 603, and a length of material 605 separating the two. Also, the stockinette 600 includes a fold 606, which can be either an accordion fold or a twist fold. In one embodiment, the fold 606 is an accordion fold, which can be oriented horizontally or vertically as the stockinette 600 is viewed in FIG. 6.

In FIG. 6, the open end 603 has been folded back over the length of material 605, thereby forming a cuff 660. In one embodiment, the cuff 660 can be formed by folding a portion 661 of the length of material 605 adjacent to the open end 603 back across the length of material 605 in a simple fold. In another embodiment, the cuff 660 can be formed by folding the portion 661 of the length of material 605 adjacent to the open end 603 back across the length of material 605 in a rolled fold or stacked fold.

When a cuff 660 is created by folding the open end 603 back across the length of material 605, an opening 662 is created that is distinct from the open end 603. The cuff 660 extends back over the length of material 605 from the opening 662 towards the closed end 604, as the portion 661 of the length of material is atop the remainder of the length of material 605. The portion 661 of the length of material can pass atop the fold 606, or it may stop short of the fold 606. For example, where the cuff 660 is created with a simple fold, the cuff 660 may extend across the fold 606. Where the cuff 660 is created with a rolled fold or stacked fold, the cuff 660 can extend across the fold 606 or stop before the fold 606.

The inclusion of a cuff 660 can be advantageous in that the hands of the person applying the stockinette 600 should generally not touch the patient during application. The inclusion of a cuff 660 permits the person applying the stockinette 600 to place their hands into the cuff 660 during application, thereby helping to maintain sterility.

Figure 7:
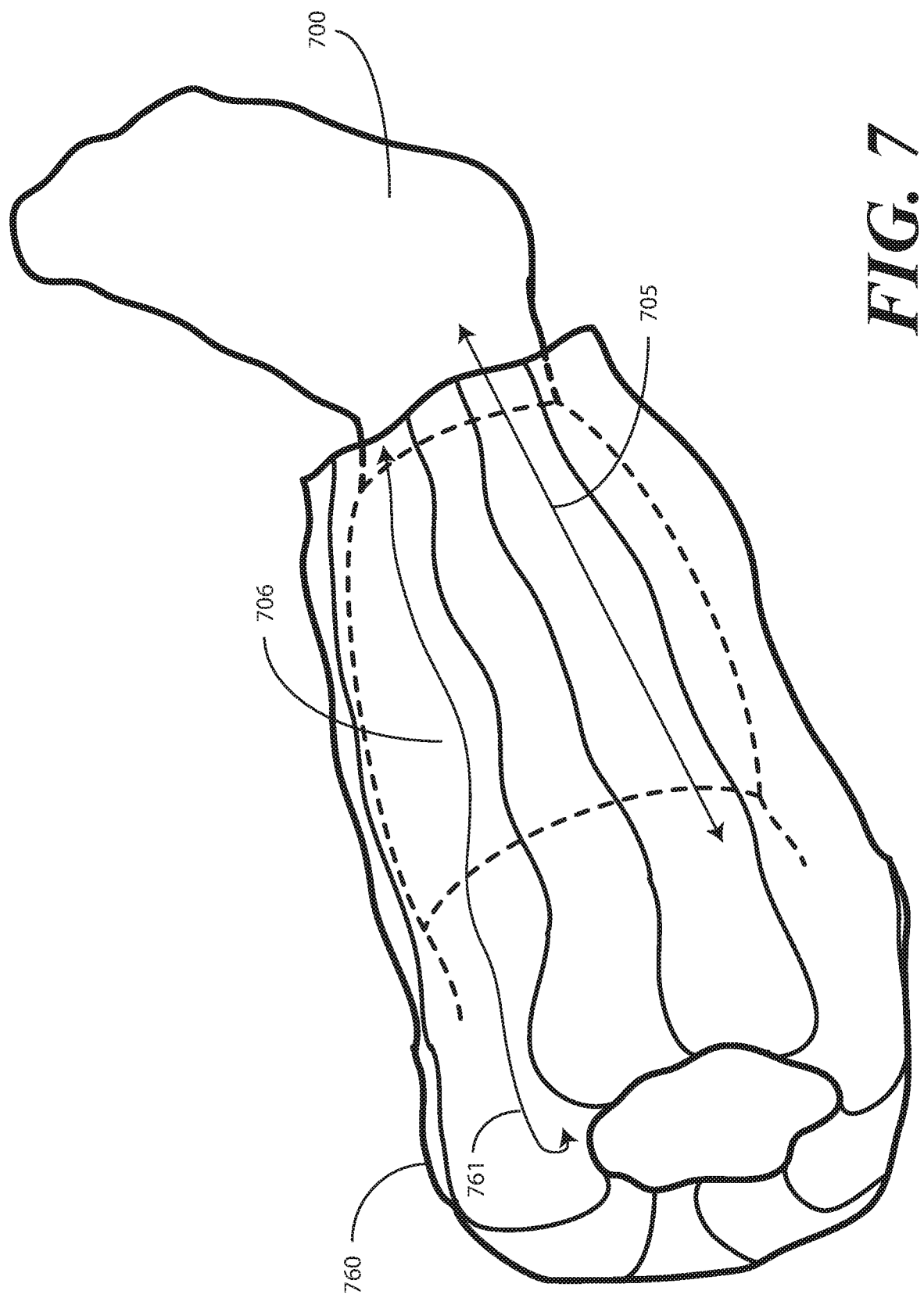
FIG. 7 illustrates one stockinette having a cuff disposed atop a fold in accordance with embodiments of the invention.

Turning now to FIG. 7, illustrated therein is a stockinette 700 having a cuff 760 that extends over the fold 706 in the length of material 705. By having the cuff 760 extend over the fold 706, which may be either of an accordion fold or a twist fold, the cuff 760 helps to maintain the integrity of the fold 706 during storage and transport. In this illustrative embodiment, the cuff 760 can be formed by simply folding down a portion 761 of the length of material 705 so as to cover and secure the fold 706.

Note that the cuffs of stockinettes as described herein may also include folds. For example, the cuff can include the primary or only fold, with the length of material remaining substantially flat. Alternatively, both the length of material and the cuff can include folds.

Figure 8:
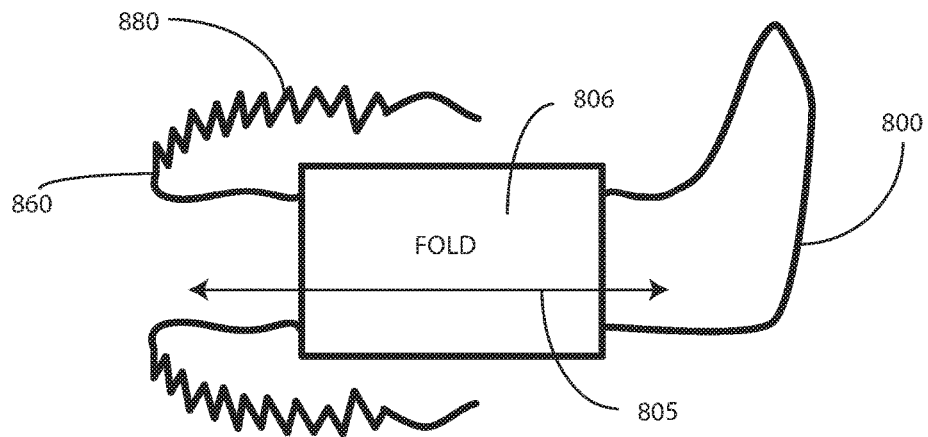
FIG. 8 illustrates one stockinette having a cuff with a fold in accordance with embodiments of the invention.

Turning now to FIG. 8, illustrated therein is one embodiment of a stockinette 800 where the cuff 860 includes a fold 880. The fold 880 in the cuff 860 in the illustrative embodiment of FIG. 8 is an accordion fold, although it will be clear to those of ordinary skill in the art having the benefit of this disclosure that the invention is not so limited. Other types of folds could be substituted for the accordion fold 880 of FIG. 8.

Additionally, the fold 880 in the cuff 860 may be the only fold in the stockinette 800. Alternatively, an optional fold 806 may also be included in the length of material 805 in addition to the fold 880 in the cuff 860. For example, it can be advantageous to only include one fold, be it the fold 880 in the cuff 860 or the optional fold 806 in the length of material 805, as the risk of a person applying the stockinette 800 inserting their hands into the wrong portion of material is reduced.

Figure 9:
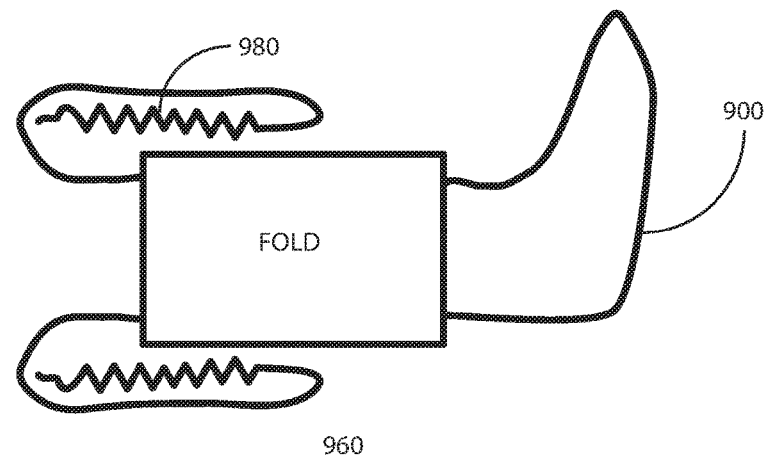
FIG. 9 illustrates another stockinette having a cuff with a fold in accordance with embodiments of the invention.
Figure 10:
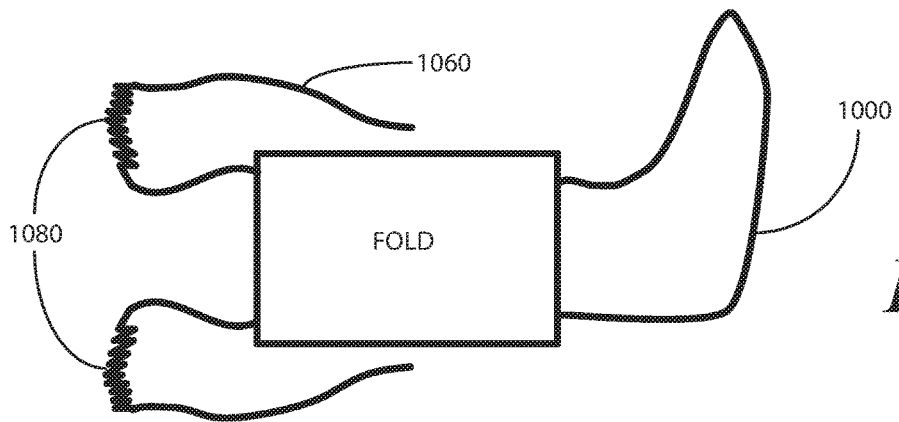
FIG. 10 illustrates another stockinette having a cuff with a fold in accordance with embodiments of the invention.

Note that just as the fold (206) along the length of material (205) can take various forms, so too can the fold in the cuff. For example, turning to FIG. 9, illustrated therein is a stockinette 900 where the cuff 960 includes an accordion fold 980 that is oriented horizontally. Turning to FIG. 10, illustrated therein is a stockinette 1000 having a cuff 1060 that includes an accordion fold 1080 that is oriented vertically. The stockinettes of FIGS. 9 and 10 can further include optional second folds along their lengths, as shown. Note also that the cuffs can cover the entirety of the stockinette, or leave a portion of the stockinette uncovered, thereby allowing a person applying the stockinette to cover a portion of a person's appendage before disengaging the various folds.

Figure 11:
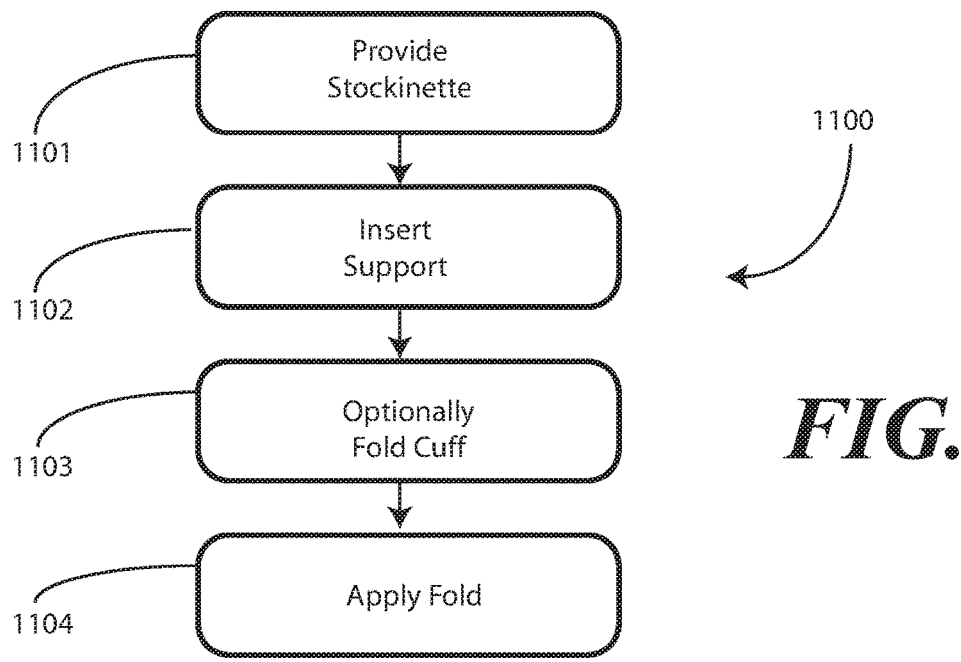
FIG. 11 illustrates a method, as a flow chart, of manufacturing a stockinette in accordance with embodiments of the invention.
Figure 12:
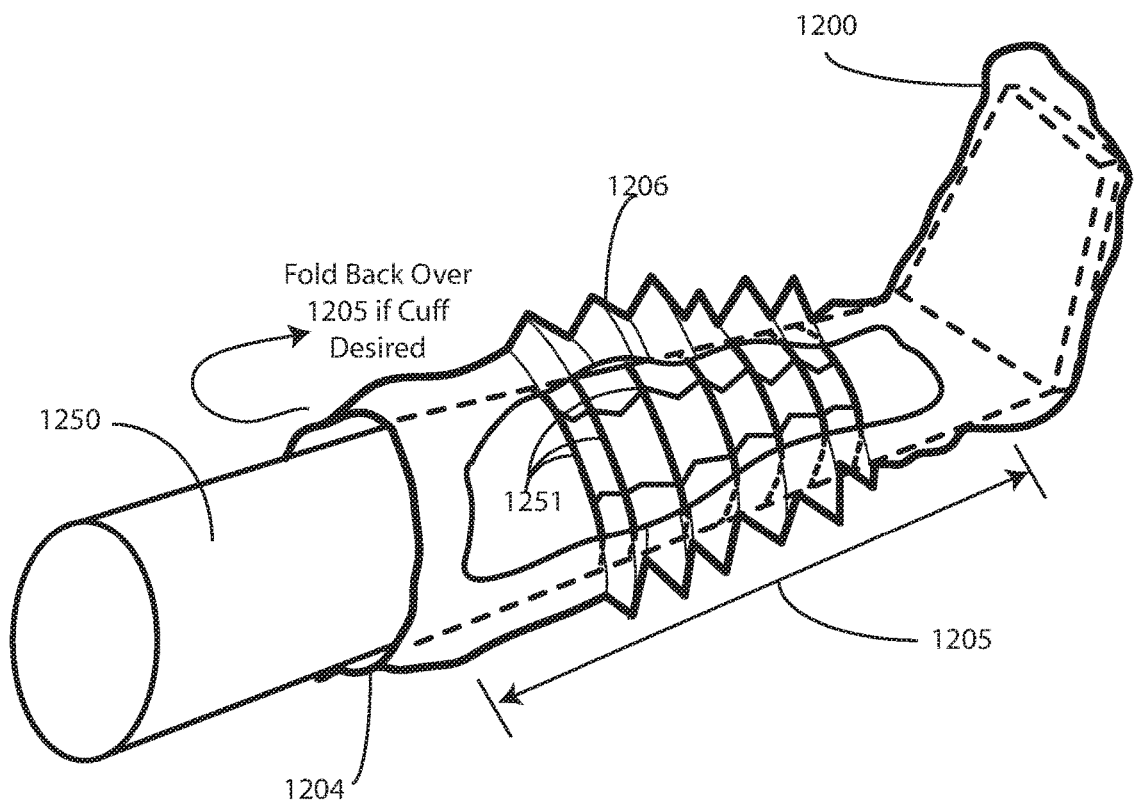
FIG. 12 illustrates, graphically, a method of manufacturing a stockinette in accordance with embodiments of the invention.

Turning now to FIGS. 11 and 12 together, illustrated therein is one method 1100 for manufacturing a stockinette in accordance with embodiments of the invention. A flow chart of the method 1100 is shown in FIG. 11, while the method 1100 is shown graphically in FIG. 12. It will be clear to those of ordinary skill in the art having the benefit of this disclosure that the various folds and various stockinettes described herein can be manufactured in a variety of ways. The illustrative method of FIGS. 11 and 12 is but one example.

In one embodiment, an expanded stockinette 1200 having an open end 1203 and a closed end 1204, each being separated from the other by a length of material 1205, is provided at step 1101. A rigid insert support 1250, which may or may not be collapsible by a spring-actuated mechanism 1251 or other folding, collapsible structure, is inserted into the stockinette 1200 at step 1101. Among other things, the rigid insert support 1250 helps the stockinette 1200 hold its shape during the folding process. The rigid insert support 1250 can also hold in place inner layers of the stockinette 1200 where the stockinette 1200 is a multilayer stockinette and the layers are not attached to each other. The rigid insert support 1250 can also provide a snag-free surface for the inner layer of the stockinette 1200.

At optional step 1102, a cuff can be formed by folding the open end 1204 back across the length of material 1205. In one embodiment, the cuff will be placed atop the fold 1206 in the length of material 1205. Where this is the case, step 1102 can occur after step 1103. However, where the cuff is not to cover the fold 1206, step 1102 can occur either before step 1103 or after step 1103. Where the cuff includes an additional fold, or where the cuff includes the only fold, the cuff can further be folded at this step. Another insert (not shown) may be placed atop the length of material 1205 and within the cuff to facilitate the cuff-folding process. As noted above, in one embodiment the cuff fold is an accordion fold.

At step 1103, a fold 1206 is applied to the length of material 1205. Where the rigid insert support 1250 is collapsible, the outer surface of the rigid insert support 1250 can be used to help in the folding process. As noted above, the fold 1206 can be an accordion fold or a twist fold. Further, the rigid insert support 1250 may be turned vertically for multi-layer stockinettes, as gravity will help to keep the closed end of the inner layer and the closed end of the outer layer together where those layers are not fully attached together. If necessary, the two open ends of the layers can be attached together at this step as well, to discourage any unwanted independent movement between layers. Note that the stockinette 1200 can be inside out on the rigid insert support 1250 as well.

Figure 13:
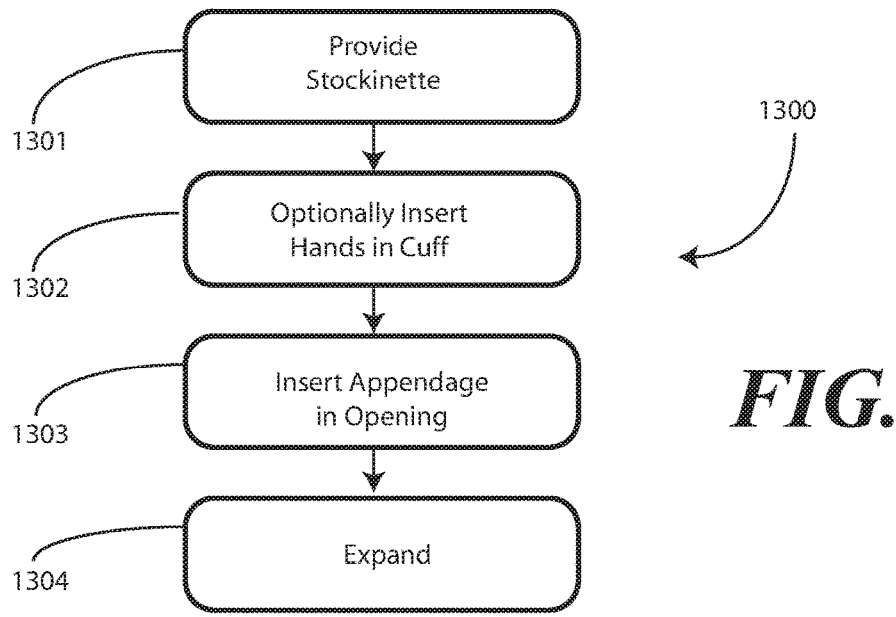
FIG. 13 illustrates a method, as a flow chart, of applying a stockinette in accordance with embodiments of the invention.
Figure 14:
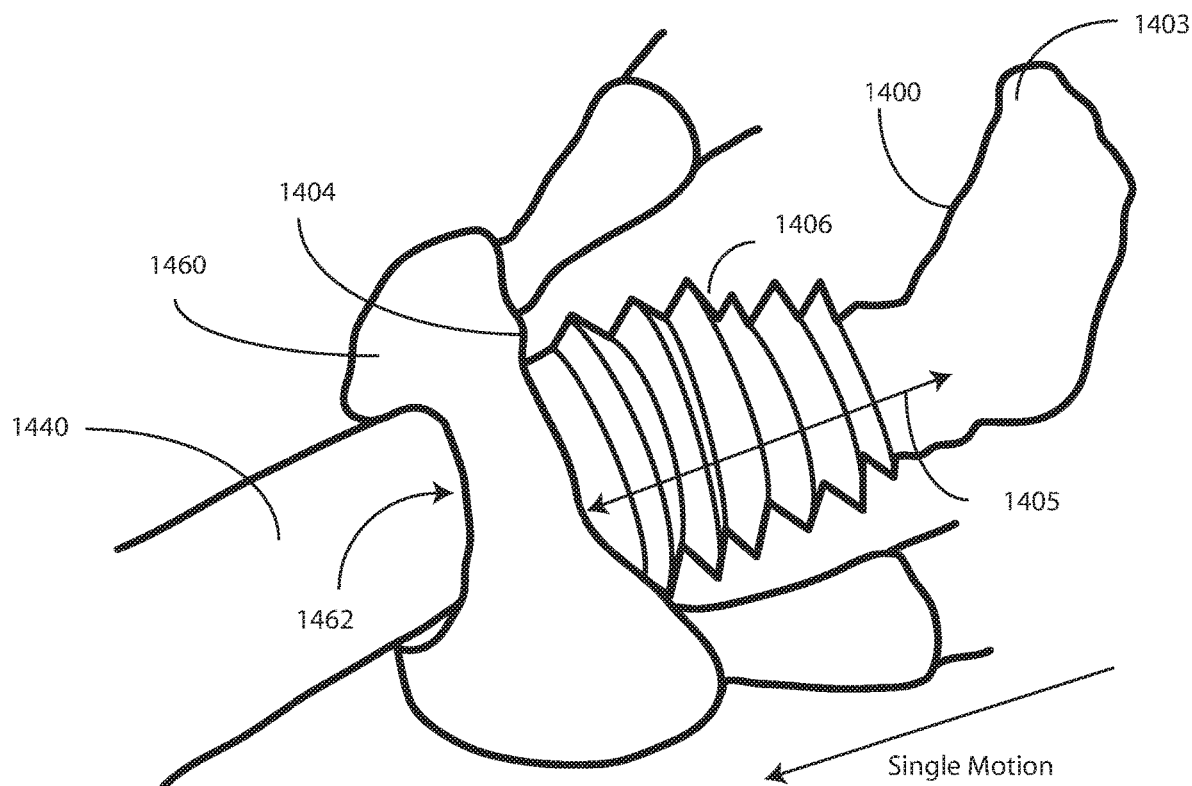
FIG. 14 illustrates, graphically, a method of applying a stockinette in accordance with embodiments of the invention.

Turning now to FIGS. 13 and 14, illustrated therein is one method 1300 for applying a stockinette in accordance with embodiments of the invention. A flow chart of the method 1300 is shown in FIG. 13, while the method 1300 is shown graphically in FIG. 14. It will be clear to those of ordinary skill in the art having the benefit of this disclosure that the stockinette 1400 of FIG. 14, as well as the other stockinettes described herein, can be applied in a variety of ways. One advantage embodiments of the present invention have over prior art stockinettes is that they can be applied by one person in one simple, continuous motion, as is shown in FIG. 14. However, the illustrative method 1300 of FIGS. 13 and 14 is but one example of an application method.

At step 1301, an expandable, surgical stockinette 1400 having an open end 1404 and a closed end 1403, each being separated by a length of material 1405, is provided. The stockinette 1400, in one embodiment, includes a fold 1406 along the length of material. The fold 1406 can be either of an accordion fold or a twist fold. Further, the stockinette 1400 may optionally include a cuff 1460, which may additionally include a fold. In one embodiment, no fold will be present in the length of material 1405. Instead, the cuff 1460 will include one or more folds.

At step 1302, the stockinette 1400 is placed on a person's appendage. This can be accomplished by at least partially inserting the appendage 1440 into an opening 1462 of the stockinette 1400. Where the stockinette 1400 includes a cuff 1460, the person applying the stockinette 1400 can also place their hands within the cuff, as shown, at this step 1302.

At step 1303, the person applying the stockinette 1400 expands the stockinette 1400 across the appendage 1440 by pulling the open end 1404 along the appendage 1440, thereby expanding the fold 1406. Where the cuff 1460 includes the only fold, pulling the open end 1404 along the appendage 1440 expands the fold in the cuff.

This step 1303 may also include at least partially unfolding the cuff 1460, where the cuff 1460 is designed to be at least partially unfolded as described above. For example, where the cuff 1460 is disposed atop the fold 1406, the person applying the cuff may optionally unfold a portion of the cuff 1460 to expose the fold 1406 prior to pulling the open end 1404 along the appendage 1440. Once the appendage 1440 is covered, the person applying the stockinette 1400 may further unfold the cuff 1460 to further cover the appendage 1440.

As described herein, an expandable stockinette having one or more folds provide a simplified application process in that one user can apply the stockinette with a single continuous motion. Further, embodiments of the present invention are generally less expensive to manufacture than are prior art stockinettes, as expensive adhesives or pull-tabs are not required.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. An expandable surgical stockinette, comprising:
   a closed end; and
   an open end for circumferentially receiving an appendage of a patient, the open end and closed end being separated by a length of material;
   wherein the length of material is folded with an accordion fold so as to be expandable by pulling the open end away from the closed end, thereby unfolding the length of material;
   wherein an opening is formed by folding the length of the material so as to extend back over itself towards the closed end so as to form a cuff extending from the opening toward the closed end; and
   wherein the cuff circumferentially covers the length of the accordion fold.

2. The expandable surgical stockinette of claim 1, wherein the accordion fold is oriented along a line defined between the closed end and the open end.

3. The expandable surgical stockinette of claim 1, wherein the accordion fold is askew relative to a line defined between the closed end and the open end.

4. The expandable surgical stockinette of claim 3, wherein the accordion fold is substantially perpendicular with the line.

5. The expandable surgical stockinette of claim 1, wherein a portion of the length of material adjacent to the open end is folded in a rolled fold.

6. The expandable surgical stockinette of claim 1, wherein the cuff is disposed atop the accordion fold.

7. The expandable surgical stockinette of claim 1, wherein the length of material is manufactured from a synthetic material.

8. The expandable surgical stockinette of claim 1, wherein the length of material is manufactured from a natural material.

9. The expandable surgical stockinette of claim 1, wherein the length of material is folded with a twist fold.

10. The expandable surgical stockinette of claim 1, wherein the length of material comprises a first layer and a second layer, wherein at least one of the first layer or the second layer is liquid impervious.

11. The expandable surgical stockinette of claim 1, wherein the length of material comprises multiple layers.

12. The expandable surgical stockinette of claim 11, wherein the multiple layers are manufactured from different materials.

13. The expandable surgical stockinette of claim 1, wherein the expandable surgical stockinette is liquid-impervious.

14. A method of applying a surgical stockinette to a patient, comprising:
- providing an expandable surgical stockinette having an open end and a closed end separated by a length of material comprising an accordion fold and a cuff, wherein the cuff circumferentially covers the length of the accordion fold;
- inserting an appendage of the patient in an opening of the expandable surgical stockinette that circumferentially receives the appendage of the patient;
- at least partially unfolding the cuff, thereby exposing the accordion fold; and
- expanding the surgical stockinette by pulling the open end along the appendage, thereby expanding the accordion fold.

15. The method of claim 14, further comprising inserting at least one hand into the cuff.

16. An expandable surgical stockinette, comprising:
- a closed end; and
- an open end for circumferentially receiving an appendage of a patient, the open end and closed being separated by a length of material;
- wherein the length of material is folded with an accordion fold so as to be expandable by pulling the open end away from the closed end, thereby unfolding the length of material;
- wherein the accordion fold is oriented substantially perpendicular relative to a line defined between the closed end and the open end;
- wherein an opening is formed by folding the length of the material so as to extend back over itself towards the closed end so as to form a cuff extending from the opening toward the closed end; and
- wherein the cuff circumferentially covers the length of the accordion fold.

17. The expandable surgical stockinette of claim 16, wherein the cuff is disposed atop the accordion fold.

18. The expandable surgical stockinette of claim 16, wherein the accordion fold is perpendicular with the line.

* * * * *